United States Patent [19]
Kuracina

[11] Patent Number: 5,269,765
[45] Date of Patent: Dec. 14, 1993

[54] METHODS OF MANUFACTURE OF SAFETY SLEEVES FOR MEDICAL INJECTION DEVICES

[75] Inventor: Thomas C. Kuracina, Ojai, Calif.

[73] Assignee: Injectimed, Inc., Ventura, Calif.

[21] Appl. No.: 850,461

[22] Filed: Mar. 10, 1992

[51] Int. Cl.⁵ .............................................. A61M 5/32
[52] U.S. Cl. .................................. 604/192; 604/198; 604/110; 604/263
[58] Field of Search ............... 604/110, 263, 192, 198

[56] References Cited

U.S. PATENT DOCUMENTS

| | | | |
|---|---|---|---|
| 2,857,912 | 10/1958 | Feinstone et al. | 604/192 |
| 4,695,274 | 9/1987 | Fox | 604/198 |
| 4,838,871 | 6/1989 | Luther | 604/192 |
| 4,927,018 | 5/1990 | Yang et al. | 206/365 |

FOREIGN PATENT DOCUMENTS 2202747 10/1988 United Kingdom ............... 604/198

Primary Examiner—C. Fred Rosenbaum
Assistant Examiner—V. Alexander
Attorney, Agent, or Firm—Donald A. Streck

[57] ABSTRACT

This invention provides alternate constructions and methods of manufacture for retractable protective sleeves used over the needle of syringes and the like. In one approach, the slats of the protective sleeve are formed by providing slots through a plastic cylinder. The base and outer end cap are then attached to the slats with adhesive or heat/sonic welding. In another approach, the cylinder includes the end cap and one of the slots extends from end to end. The needle is mounted in a cylindrical plug. For assembly, the cylinder is unrolled and the needle/plug are inserted from the side rather than from an end. The cylinder is then re-rolled and inserted into the base. The end cap is secure with a cylindrical collar. The base can be a stand-alone piece or built into the end of a syringe or other similar medical device employing the needle.

9 Claims, 4 Drawing Sheets

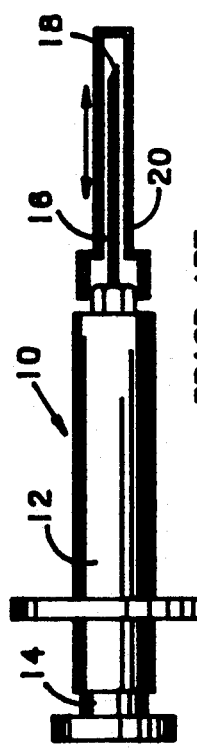
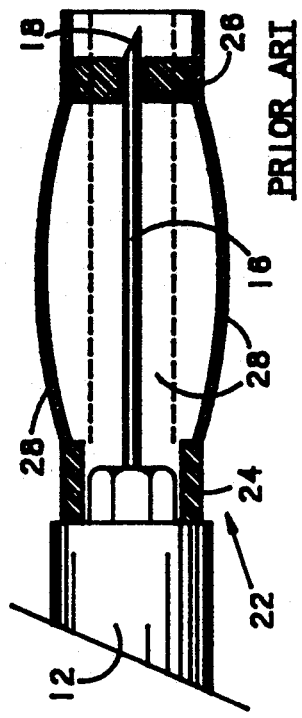
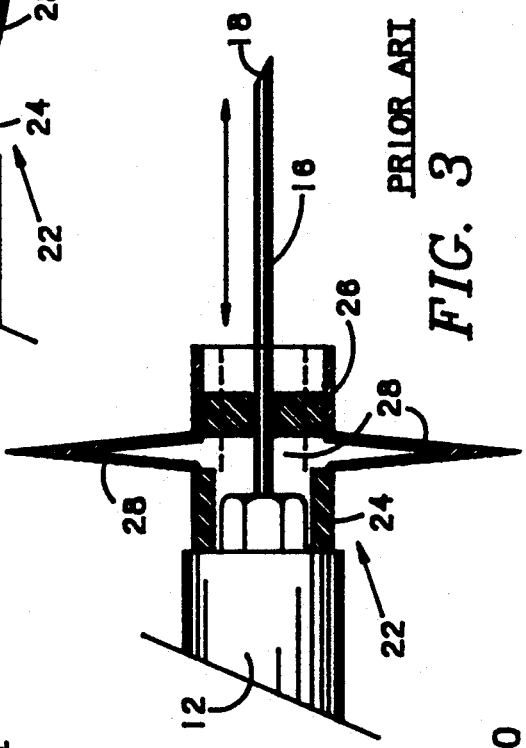
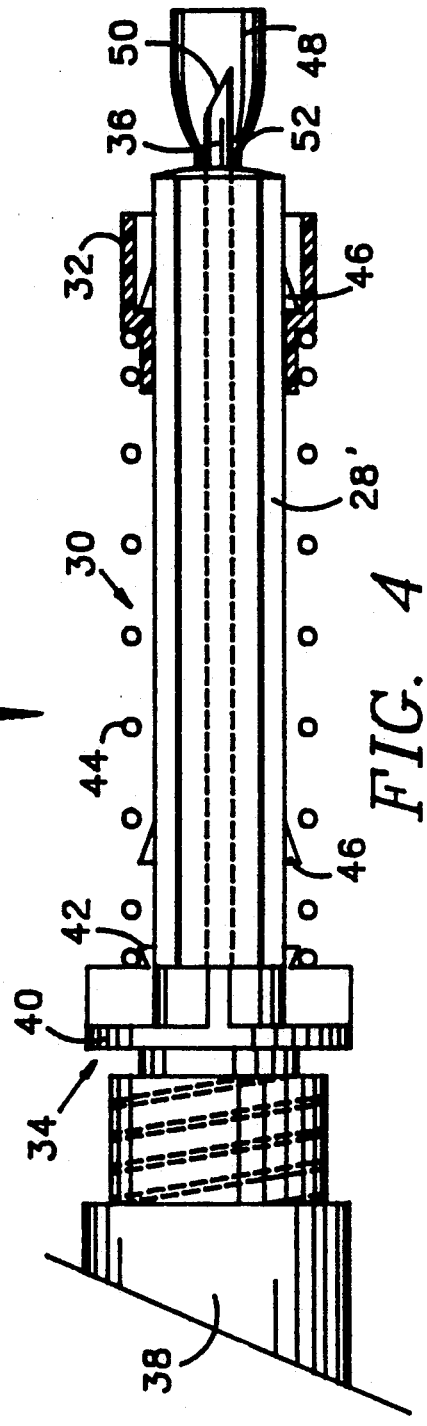
FIG. 1 PRIOR ART
FIG. 2 PRIOR ART
FIG. 3 PRIOR ART
FIG. 4

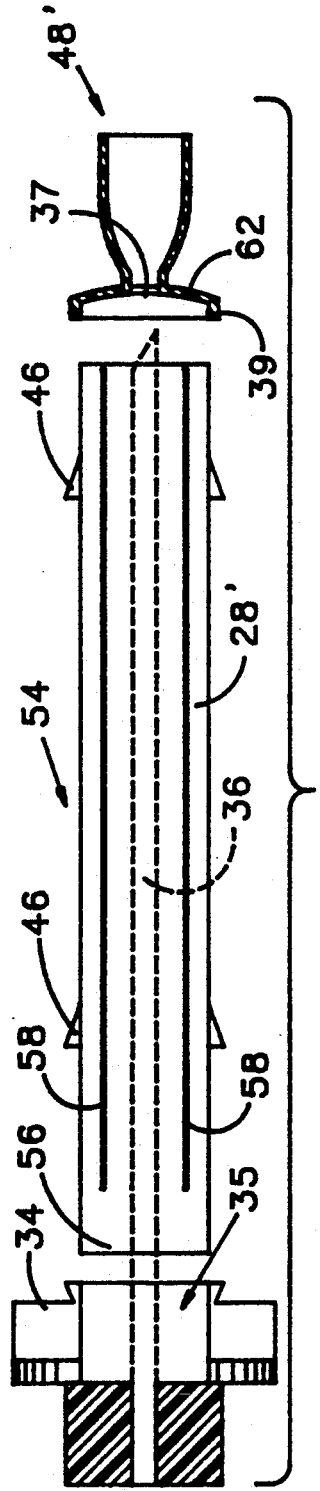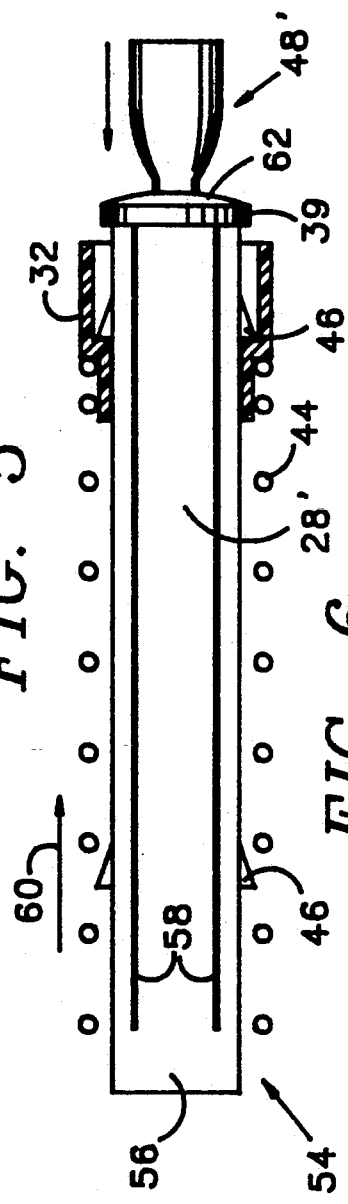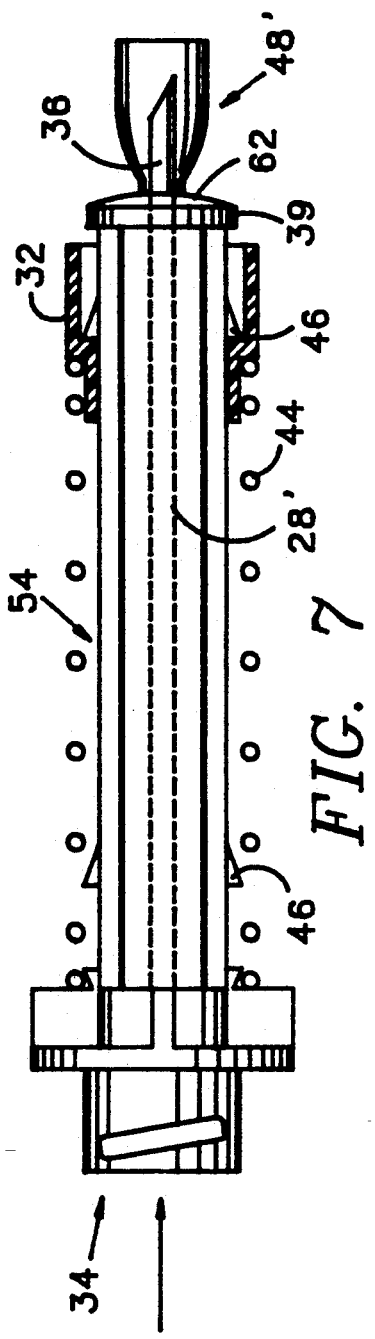

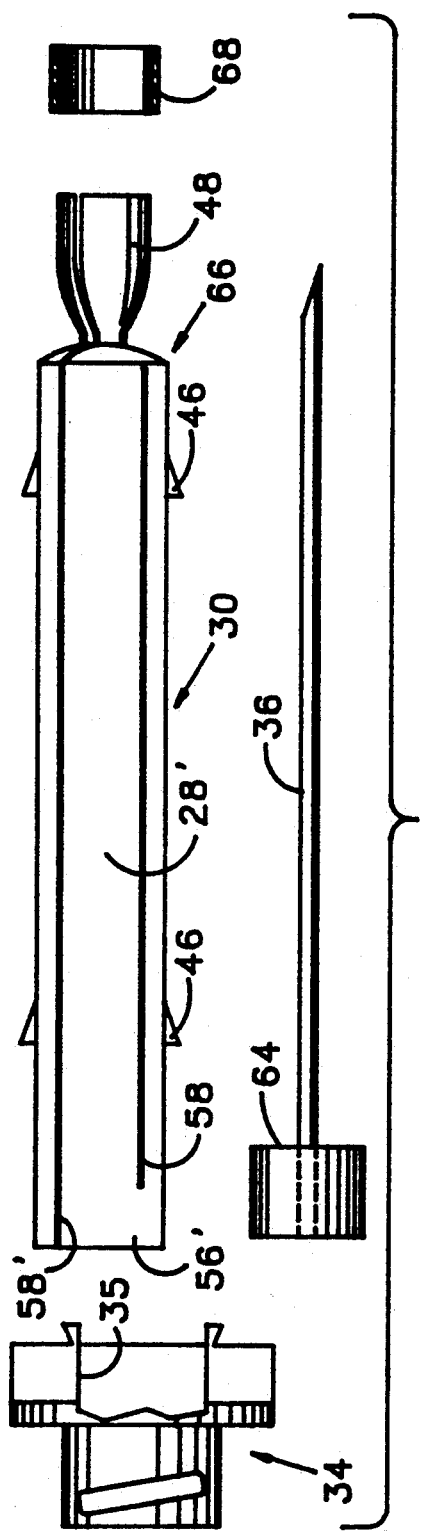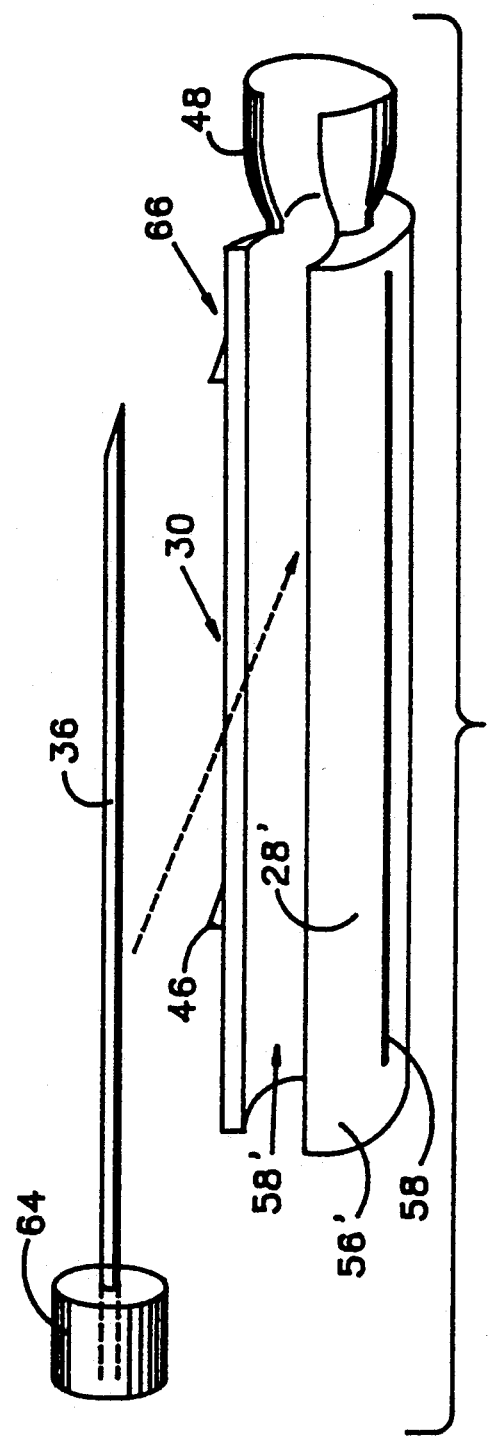

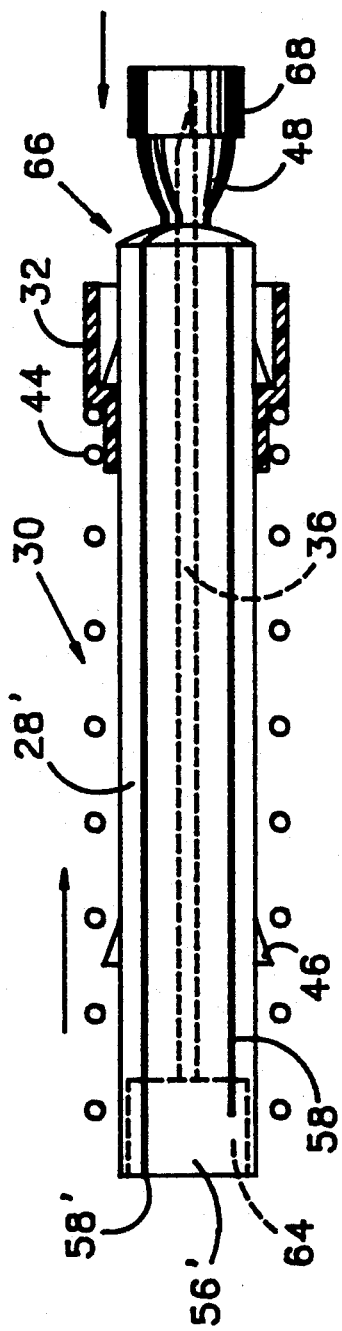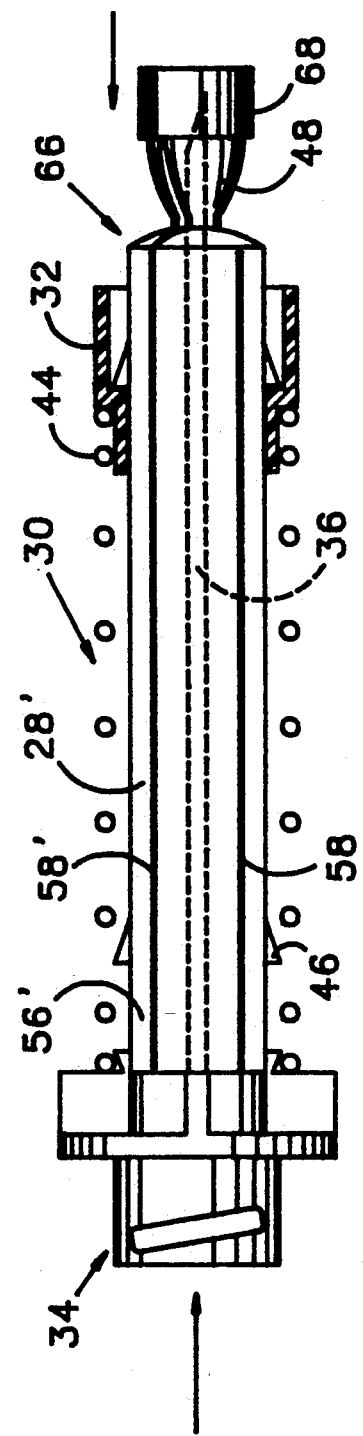

METHODS OF MANUFACTURE OF SAFETY SLEEVES FOR MEDICAL INJECTION DEVICES

BACKGROUND OF THE INVENTION

This invention relates to medical devices for injecting living bodies and, more particularly, to safety features incorporated therewith. In particular, it relates to alternate constructions and methods of manufacture for retractable protective sleeves used over the needle of syringes and the like.

In U.S. Pat. No. 4,998,922 by Thomas C. Kuracina entitled SAFETY SYRINGE CAP MINIMIZING NEEDLE-STICK PROBABILITY which issued Mar. 12, 1991, a safety device for hypodermic needles and the like is shown. The inventions shown hereinafter are improvements thereto by inventors including and/or working with Mr. Kuracina. In the interest of simplicity herein, the teachings of that patent are incorporated herein by reference and the discussion of the background art will be kept to a minimum.

A typical prior art hypodermic syringe 10 as shown in FIG. 1 includes a barrel 12 having a moving plunger 14 therein. A needle 16 having a sharp beveled tip 18 extends from the end opposite the end of the barrel 12 into which the plunger 14 is inserted. The needle 16 is covered by a removeable cap 20 for safety purposes. The problem to be solved and avoided is the accidental sticking of users of the syringe 10 by the tip 18 after use where the tip 18 may carry body fluids containing agents of hepatitis B, AIDS, and the like. Accidental needle stick is a very common problem in the health care industry and besides the risk of serious illness or even death as a result thereof, the insurance industry spends over a billion dollars a year in the testing of individuals who have been subjected to post-use needle stick.

The 1979 patent of Alvarez proposed a retractable plastic protective sleeve 22 as depicted in FIGS. 2 and 3. The Alvarez sleeve 22 has an inner hub 24 which fits around the base of the needle 16 and an outer hub 26 through which the tip 18 passes. The inner and outer hubs 24, 26 are connected by curved slats 28. When the needle 16 is to be inserted into the body of a patient, the force required to move the sleeve 22 from its extended position of FIG. 2 to its retracted position of FIG. 3 is as depicted in the graph of FIG. 4. Thus, there is really no actually safety from a large variety of ways in which accidental needle stick takes place. Even if the sleeve 22 fully extends after use, a slight blow against a user or observer in the area will cause the sleeve 22 to retract and the tip 18 to stick the unfortunate person.

A Kuracina protective sleeve 30 in a preferred embodiment is depicted in FIG. 4. The slats 28' are transversely curved to cause a high degree of force to be required to move the protective sleeve 30 from its extended position covering the tip. Moreover, a spring-biased locking collar 32 is added over the protective sleeve 30, which all but prevents the protective sleeve 30 from moving from its extended position covering the tip. The locking collar 32 must be moved from its locked position to a retracted, unlocked position before the unique deformation qualities of the sleeve 30 take effect. After use, the locking collar 32 springs back to its locked position. Thus, in virtually all "accidental" contact with the tip end of a hypodermic syringe, actual penetration by the tip should be prevented.

As originally disclosed, the Kuracina protective sleeve is shown as a unitary device made in a single injection molding process and assembled over an associated needle from the tip end of the needle. The inventions described hereinafter are intended to provide alternate methods of constructing and manufacturing the Kuracina protective sleeve to attain certain benefits to be described and as will be recognized by those skilled in the art.

Other objects and benefits of the inventions disclosed herein will become apparent from the detailed description which follows hereinafter when taken in conjunction with the drawing figures which accompany it.

SUMMARY

The foregoing object has been achieved by the method of construction and assembly of a retractable protective sleeve for a needle in a medical device comprising a plurality of longitudinal slats extending between a base and an end piece of the present invention comprising the steps of, providing a plastic cylinder having a plurality of longitudinal slots through sidewalls thereof to create a plurality of longitudinal slats extending between cylindrical end portions; providing a base member having a concentric longitudinal cylindrical bore therethrough, the bore having a cylinder-receiving portion on an end thereof having an inside diameter substantially equal to an outside diameter of the plastic cylinder; providing an end piece member having a concentric needle-receiving bore therethrough of a diameter to slideably receive the needle and a cap portion concentrically surrounding the needle-receiving bore, the cap portion including an outer rim having an inside diameter substantially equal to the outside diameter of the plastic cylinder; inserting one end of the plastic cylinder into the cylinder-receiving portion of the base portion and permanently affixing it therein; and, inserting an opposite end of the plastic cylinder into the cap portion of the end piece and permanently affixing it therein.

Where the retractable protective sleeve further includes a locking collar and spring which slidably fit over the plastic cylinder and the longitudinal slats have projections for interacting with the locking collar extending outward therefrom, before steps resulting in the plastic cylinder having both ends covered with the base portion and the end piece, respectively, sliding the locking collar and spring over the plastic cylinder from an uncovered end thereof.

The method may also comprise the additional step of first molding a base portion of the needle into a needle-holding portion of the concentric longitudinal cylindrical bore adjacent the cylinder-receiving portion.

The foregoing object has also been achieved by the method of construction and assembly of a retractable protective sleeve for a needle in a medical device comprising a plurality of longitudinal slats extending between a base and an end piece of the present invention comprising the steps of, providing a plastic cylinder having a plurality of longitudinal slots through sidewalls thereof to create a plurality of longitudinal slats extending between first and second cylindrical end portions wherein a first cylindrical end portion is the end piece having a cylindrical end portion for covering a tip of the needle and one of the plurality of longitudinal slots extends through both cylindrical end portions whereby the plastic cylinder can be unrolled towards a flattened shape; providing a base member having a concentric longitudinal cylindrical bore therethrough, the bore having a cylinder-receiving portion on an end thereof having an inside diameter substantially equal to an outside diameter of the plastic cylinder at a second cylindrical end portion; providing a needle assembly wherein a base portion of the needle is concentrically carried by a cylindrical member having an outside diameter substantially equal to an inside diameter of the plastic cylinder at the second cylindrical end portion; providing a cylindrical collar having an inside diameter substantially equal to an outside diameter of the cylindrical end portion of the end piece; unrolling the plastic cylinder towards a flattened shape to open the one of the plurality of longitudinal slots which extends through both cylindrical end portions an amount sufficient for the cylindrical member to pass therethrough; inserting the cylindrical member and the needle in combination laterally through the one of the plurality of longitudinal slots which extends through both cylindrical end portions to place the cylindrical member within the second cylindrical end portion with a free end of the needle extending longitudinally down the plastic cylinder towards and into the first cylindrical end portion; re-rolling the plastic cylinder around the cylindrical member and the needle in combination and permanently affixing the cylindrical member therein; inserting one end of the plastic cylinder into the cylinder-receiving portion of the base portion and permanently affixing it therein; and, inserting the cylindrical end portion of the end piece into the cylindrical collar and permanently affixing it therein.

Again, where the retractable protective sleeve further includes a locking collar and spring which slidably fit over the plastic cylinder and the longitudinal slats have projections for interacting with the locking collar extending outward therefrom the method may additionally include the assembly step of sliding the locking collar and spring over the plastic cylinder from an unblocked end thereof.

DESCRIPTION OF THE DRAWINGS

FIG. 1 is a simplified, partially cutaway drawing of a prior art hypodermic syringe with a removeable protective cap.

FIG. 2 is a simplified, partially cutaway drawing of the front portion of a hypodermic syringe with a prior art retractable protective sleeve over the needle thereof in its extended position.

FIG. 3 is a simplified, partially cutaway drawing of the front portion of a hypodermic syringe with a prior art retractable protective sleeve over the needle thereof as in FIG. 2 with the sleeve in its retracted position.

FIG. 4 is a simplified, partially cutaway drawing of the front portion of a hypodermic syringe with a Kuracina type retractable protective sleeve over the needle thereof in its extended and locked position.

FIG. 5 is an exploded view of the components of a first embodiment of construction and assembly of a Kuracina type retractable protective sleeve according to the present invention.

FIGS. 6 and 7 show possible steps in the assembly of the components of FIG. 5.

FIG. 8 is an exploded view of the components of a second embodiment of construction and assembly of a Kuracina type retractable protective sleeve according to the present invention.

FIGS. 9 through 11 show possible steps in the assembly of the components of FIG. 8.

DESCRIPTION OF THE PREFERRED EMBODIMENTS:

As depicted in FIG. 4, a Kuracina type retractable protective sleeve 30 typically includes a base hub portion 34 which carries the needle 36, provides a means for attachment to a syringe 38 or other needle-oriented medical device, provides a hub at 40 for the removable attachment of a hard cover (not shown), provides a means such as the gripping tabs 42 for gripping the inner end of the spring 44, and attaches to the inner end of the slats 28'. The slats 28' include projections 46 for preventing the locking collar 32 from coming off the end of the slats 28' and for releasably locking the collar 32 in its retracted and unlocked position. At their outer end, the slats 28' terminate in an end piece which is preferably a transparent bell end 48 which covers the tip 50 while allowing its shape and condition to be viewed. When the foregoing components of the Kuracina type retractable protective sleeve 30 are injection molded as a single unit, there are several limitations imposed. The needle 36 must be molded into a separate piece that is then mounted within the base hub portion 34. The needle 36 must be inserted along the length of the slats 28' from the base hub portion 34 and through a small bore 52 leading to the bell end 48. Finally, the spring 44 and locking collar 32 must be mounted over the protective sleeve 30 from the bell end 48 and over the front projections 46 by deforming the slats 28' inward at their front end.

As an alternate approach with certain advantages, the components of the Kuracina type retractable protective sleeve 30 can be separately molded as depicted in FIG. 5. In other words, the base hub portion 34, a slat assembly 54, and the bell end 48' are separate items. If desired, the needle 36 can also be molded directly into the base hub portion 34 to save a component and an extra assembly step. Actual assembly can take place in various ways depending on the primary objectives and improvements to be attained. One way is shown in the drawings of FIGS. 6 and 7. The slat assembly 54 is basically a cylinder 56 having the slats 28' separated by slots 58. The base hub portion 34 has a bore therethrough having a portion 35 on its inner end of a diameter substantially equal to that of the slat assembly 54 into which the slat assembly 54 can be slid during assembly. Similarly, the bell end 48' has a bore 37 therethrough in the usual manner for slidably receiving the needle 36 as well as a cap portion 62 concentrically surrounding the bore 37 having a peripheral rim 39 of an inside diameter substantially equal to that of the slat assembly 54 into which the slat assembly 44 can be slid during assembly. The locking collar 32 and spring 44 can be slid over the slat assembly 54 from the inner end as indicated by the arrow 60. This is easy at this point since the slat assembly 54 in its original condition is more flexible and it is easier to move the inner projections 46 inward. The bell end 48' can then be attached by using adhesive or heat/sonic welding to attach the cap portion 62 of the bell end 48' to the outer end of the slat assembly 54. The base hub portion 34 can then be attached to the inner end of the slat assembly 54 using adhesive or heat/sonic welding. The needle 36 can then be mounted; or, if molded into the base hub portion 34, it is positioned at the time of attaching the base hub portion 34. If it is more important to be able to position the tip 50 of the needle 36 through the bore 52 leading to the bell end 48', the base hub portion 34 and needle 36 should be attached to the slat assembly 54 first. The bell end 48' can then be positioned over the exposed tip 50 of the needle 36 after the spring 44 and locking collar 32 have been slid over the outer end of the slat assembly 54.

An alternate construction and assembly approach which does not require any sliding of the needle 36 through the protective sleeve 30 is shown in FIGS. 8-11. In this case, the protective sleeve 30 comprises the individually-molded components shown in FIG. 8. In particular, there is a base hub portion 34 as in the previous embodiment. The needle 36 is carried by a cylindrical needle hub 64. There is a combined slat and bell end assembly 66 and a cylindrical collar 68. The combined slat and bell end assembly 66 is a cylinder 56' having the slats 28' separated by slots 58 and the bell end 48 molded as an integral part of one end. One of the slots 58' extends longitudinally from end-to-end through the bell end 48 so that the combined slat and bell end assembly 66 can be unrolled to widen the slot 58' as depicted in FIG. 9. The cylindrical needle hub 64 is of an outside diameter equal to the inside diameter of the combined slat and bell end assembly 66 at the end opposite the bell end 48. The cylindrical collar 68 is of an inside diameter equal to the outside diameter of the bell end 48.

To assemble the above-described components, the combined slat and bell end assembly 66 is unrolled to widen the slot 58' and the needle 36 and cylindrical needle hub 64 in combination are inserted through the slot sideways as depicted in FIG. 9. The spring 44 and locking collar 32 can then be slid on from the end opposite the bell end 48 and the collar 68 slid on over the bell end 48 as depicted in FIG. 10. Assembly can then be completed by adding the base hub portion 34. If desired of course, the base hub portion 34 could be positioned first followed by the spring 44, locking collar 32, and collar 68. The components are permanently assembled in the usual manner by adhesive or heat/sonic welding.

As those skilled in the art will readily recognize and appreciate, both of the foregoing methods of construction and assembly can be accomplished when the base hub portion is actually built into or integrally formed as part of the needleholding end of the barrel of a syringe or the like.

Wherefore, having thus described the present invention,

What is claimed is:

1. A method of construction and assembly of a retractable protective sleeve for a needle in a medical device comprising a plurality of deformable longitudinal slats extending between a base and an end piece comprising the steps of:
   a) providing a plastic cylinder having a plurality of longitudinal slots through sidewalls thereof to create a plurality of longitudinal slats extending between first and second ends of the plastic cylinder;
   b) providing a base member having a concentric longitudinal cylindrical bore therethrough, the bore having a cylinder-receiving portion on an end thereof having an inside diameter substantially equal to an outside diameter of the plastic cylinder;
   c) providing an end piece member having a concentric needle-receiving bore therethrough of a diameter to slideably receive the needle and a cap portion concentrically surrounding the needle-receiving bore, the cap portion including an outer rim having an inside diameter substantially equal to the outside diameter of the plastic cylinder;
   d) inserting said first end of the plastic cylinder into the cylinder-receiving portion of the base portion and permanently affixing it therein; and,
   e) inserting said second end of the plastic cylinder into the cap portion of the end piece and permanently affixing it therein.

2. The method of construction and assembly of a retractable protective sleeve for a needle in a medical device of claim 1 wherein:
   a) the retractable protective sleeve further includes a locking collar and spring which slidably fit over the plastic cylinder; and,
   b) the longitudinal slats have projections for interacting with the locking collar extending outward therefrom; and additionally including the assembly, step of,
   c before both steps (d) and (e), sliding the locking collar and spring over the plastic cylinder from one of (i) the first end, and (ii) the second end.

3. The method of construction and assembly of a retractable protective sleeve for a needle in a medical device of claim 1 wherein said step (b) of providing a base member comprises the additional step of:
   molding a base portion of the needle into a needle-holding portion of the concentric longitudinal cylindrical bore adjacent the cylinder-receiving portion.

4. A method of construction and assembly of a retractable protective sleeve for a needle in a medical device comprising a plurality of deformable longitudinal slats extending between a base and an end piece comprising the steps of:
   a) providing a plastic cylinder having a plurality of longitudinal slots through sidewalls thereof to create a plurality of longitudinal slats extending between first and second ends of the plastic cylinder wherein the first end is the end piece having a cylindrical projection for covering a tip of the needle and one of the plurality of longitudinal slots extends through the first and second ends of the plastic cylinder whereby the plastic cylinder can be unrolled towards a flattened shape;
   b) providing a base member having a concentric longitudinal cylindrical bore therethrough, the bore having a cylinder-receiving portion on an end thereof having an inside diameter substantially equal to an outside diameter of the plastic cylinder at the second end;
   c) providing a needle assembly wherein a base portion of the needle is concentrically carried by a cylindrical member having an outside diameter substantially equal to an inside diameter of the plastic cylinder at the second end;
   d) providing a cylindrical collar having an inside diameter substantially equal to an outside diameter of the cylindrical projection of the end piece;
   e) unrolling the plastic cylinder towards a flattened shape to open the one of the plurality of longitudinal slots which extends through the first and second ends of the plastic cylinder an amount sufficient for the cylindrical member to pass therethrough;
   f) inserting the cylindrical member and the needle in combination laterally through the one of the plurality of longitudinal slots which extends through the first and second ends of the plastic cylinder to place the cylindrical member within the second end of the plastic cylinder with a free end of the needle extending longitudinally down the plastic cylinder towards and into the first end of the plastic cylinder;

g) re-rolling the plastic cylinder around the cylindrical member and the needle in combination and permanently affixing the cylindrical member therein;

h) inserting the second end of the plastic cylinder into the cylinder-receiving portion of the base portion and permanently affixing it therein; and, i) inserting the cylindrical projection of the end piece into the cylindrical collar and permanently affixing it therein.

5. The method of construction and assembly of a retractable protective sleeve for a needle in a medical device of claim 4 wherein:

a) the retractable protective sleeve further includes a locking collar and spring which slidably fit over the plastic cylinder; and, b) the longitudinal slats have projections for interacting with the locking collar extending outward therefrom; and additionally including the assembly step of, c) before both steps (h) and (i), sliding the locking collar and spring over the plastic cylinder from one of (i) the first end, and (ii) the second end.

6. In a syringe having a barrel with a needle-holding end carrying a needle, a method of construction and assembly of a retractable protective sleeve for the needle comprising a plurality of deformable longitudinal slats extending between a base and an end piece comprising the steps of:

a) providing a plastic cylinder having a plurality of longitudinal slots through sidewalls thereof to create a plurality of longitudinal slats extending between first and second ends of the plastic cylinder;

b) providing a base member as part of the needle-holding end, the base member having a concentric longitudinal cylindrical bore therethrough having an inner portion for receiving and holding a base portion of the needle and a cylinder-receiving outer portion having an inside diameter substantially equal to an outside diameter of the plastic cylinder;

c) providing an end piece member having a concentric needle-receiving bore therethrough of a diameter to slideably receive the needle and a cap portion concentrically surrounding the needle-receiving bore, the cap portion including an outer rim having an inside diameter substantially equal to the outside diameter of the plastic cylinder;

d) inserting said first end of the plastic cylinder into the cylinder-receiving portion of the base portion and permanently affixing it therein; and, e) inserting said second end of the plastic cylinder into the cap portion of the end piece and permanently affixing it therein.

7. The method of construction and assembly of a retractable protective sleeve for the needle of a syringe of claim 6 wherein:

a) the retractable protective sleeve further includes a locking collar and spring which slidably fit over the plastic cylinder; and, b) the longitudinal slats have projections for interacting with the locking collar extending outward therefrom; and additionally including the assembly step of, c) before both steps (d) and (e), sliding the locking collar and spring over the plastic cylinder from one of (i) the first end, and (ii) the second end.

8. In a syringe having a barrel with a needle-holding end carrying a needle, a method of construction and assembly of a retractable protective sleeve for the needle comprising a plurality of deformable longitudinal slats extending between a base and an end piece comprising the steps of:

a) providing a plastic cylinder having a plurality of longitudinal slots through sidewalls thereof to create a plurality of longitudinal slats extending between first and second ends of the plastic cylinder wherein the first end is the end piece having a cylindrical projection for covering a tip of the needle and one of the plurality of longitudinal slots extends through the first and second ends of the plastic cylinder whereby the plastic cylinder can be unrolled towards a flattened shape;

b) providing a base member as part of the needle-holding end, the base member having a concentric longitudinal cylindrical bore therethrough having an inner portion for receiving and holding a base portion of the needle and a cylinder-receiving outer portion having an inside diameter substantially equal to an outside diameter of the plastic cylinder;

c) providing a needle assembly wherein a base portion of the needle is concentrically carried by a cylindrical member having an outside diameter substantially equal to an inside diameter of the plastic cylinder at the second end;

d) providing a cylindrical collar having an inside diameter substantially equal to an outside diameter of the cylindrical projection of the end piece;

e) unrolling the plastic cylinder towards a flattened shape to open the one of the plurality of longitudinal slots which extends through the first and second ends of the plastic cylinder an amount sufficient for the cylindrical member to pass therethrough;

f) inserting the cylindrical member and the needle in combination laterally through the one of the plurality of longitudinal slots which extends through the first and second ends of the plastic cylinder to place the cylindrical member within the second end of the plastic cylinder with a free end of the needle extending longitudinally down the plastic cylinder towards and into the first end of the plastic cylinder;

g) re-rolling the plastic cylinder around the cylindrical member and the needle in combination and permanently affixing the cylindrical member therein;

h) inserting the second end of the plastic cylinder into the cylinder-receiving portion of the base portion and permanently affixing it therein; and, i) inserting the cylindrical projection of the end piece into the cylindrical collar and permanently affixing it therein.

9. The method of construction and assembly of a retractable protective sleeve for a needle in a medical device of claim 8 wherein:

a) the retractable protective sleeve further includes a locking collar and spring which slidably fit over the plastic cylinder; and, b) the longitudinal slats have projections for interacting with the locking collar extending outward therefrom; and additionally including the assembly step of, c) before both steps (h) and (i), sliding the locking collar and spring over the plastic cylinder from one of (i) the first end, and (ii) the second end.

* * * * *